United States Patent [19]

Shikinami et al.

[11] Patent Number: 4,981,689

[45] Date of Patent: Jan. 1, 1991

[54] INSECT REPELLENT MATERIAL CONTAINING AMIDE INGREDIENT, CHLORINATED POLYETHYLENE AND ELASTOMER

[75] Inventors: Yasuo Shikinami; Kunihiro Hata, both of Osaka; Hiroshi Kimura, Ako; Kiyoshi Utsumi, Aiori, all of Japan

[73] Assignees: Takiron Co., Ltd., Osaka; Earth Chemical Co., Ltd, Ako, both of Japan

[21] Appl. No.: 532,125

[22] Filed: Jun. 1, 1990

Related U.S. Application Data

[63] Continuation-in-part of Ser. No. 294,042, Feb. 4, 1989, abandoned, which is a continuation-in-part of Ser. No. 91,347, Aug. 27, 1987, abandoned, which is a continuation of Ser. No. 758,642, Jul. 11, 1985, abandoned.

[30] Foreign Application Priority Data

Dec. 29, 1983 [JP] Japan ............................. 58-249000
Feb. 20, 1984 [JP] Japan ............................. 59-23700[U]

[51] Int. Cl.$^5$ ............................................. A01N 25/08
[52] U.S. Cl. ....................................... 424/409; 424/78; 424/83
[58] Field of Search ......................... 424/78, 83, 409

[56] References Cited

U.S. PATENT DOCUMENTS

| | | | |
|---|---|---|---|
| 3,873,725 | 3/1975 | Skinner et al. | 424/DIG. 10 |
| 3,876,762 | 4/1975 | Rabussier et al. | 424/78 |
| 4,195,075 | 3/1980 | Miller | 424/16 |
| 4,536,388 | 8/1985 | Pearce, III | 424/16 |
| 4,543,367 | 9/1985 | Rutherford | 424/78 |
| 4,908,208 | 3/1990 | Lee et al. | 424/409 |

FOREIGN PATENT DOCUMENTS 1326825 8/1973 United Kingdom .

*Primary Examiner*—Thurman K. Page
*Assistant Examiner*—Robert H. Harrison
*Attorney, Agent, or Firm*—Moonray Kojima

[57] ABSTRACT

This invention relates to a repellent material comprising an amide type repelling ingredient, a chlorinated polyethylene and a thermoplastic elastomer, and more particularly to an insect repellent material for preventing insects such as flies, mites, cockroaches and other insects from invading into electronic balances, telephones, computers, facsimiles, automatic vending machines and others in kitchens, foodshops, food storages, foodfirms, or offices, clean rooms, which has an excellent repelling effect to the insects, the repelling effect being controllable for a long period of time in view of using aims.

5 Claims, 3 Drawing Sheets

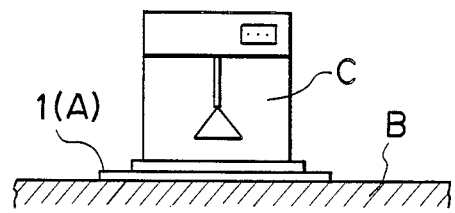
FIG_1
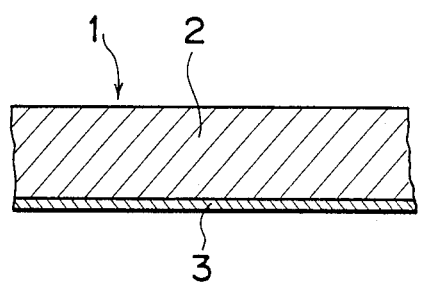
FIG_2(A)
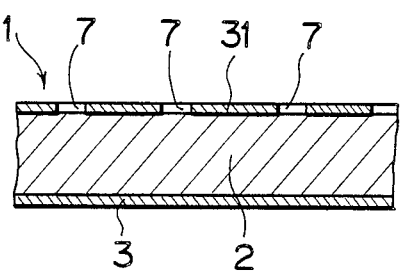
FIG_2(B)
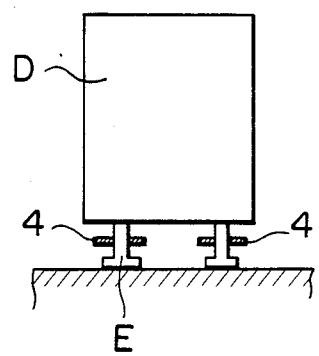
FIG_3
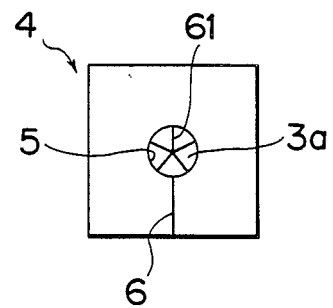
FIG_4

FIG_5
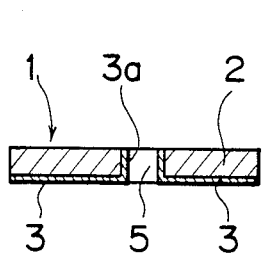
FIG_6
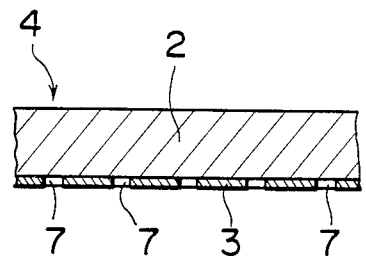
FIG_7
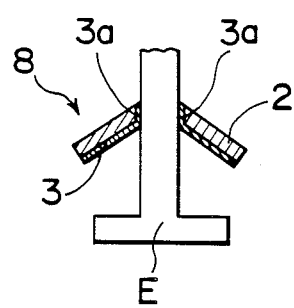
FIG_8
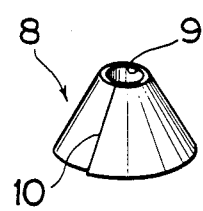
FIG_9
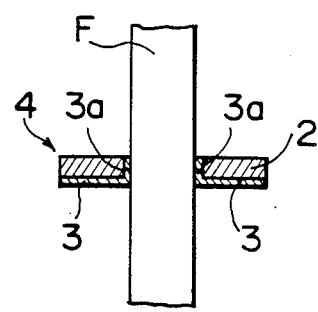
FIG_10
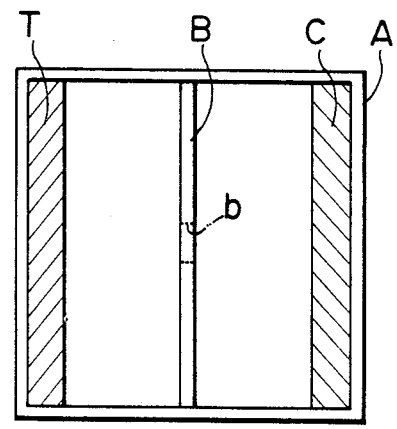

FIG_11
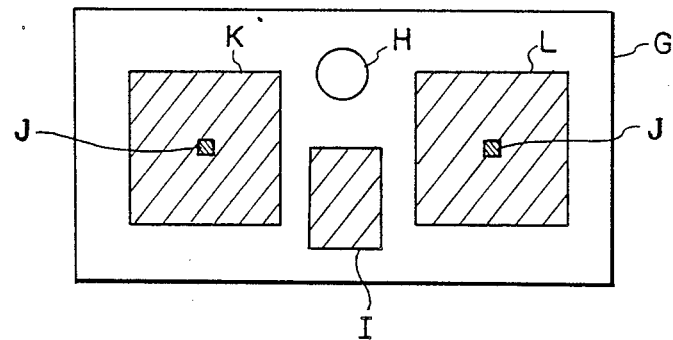
FIG_12
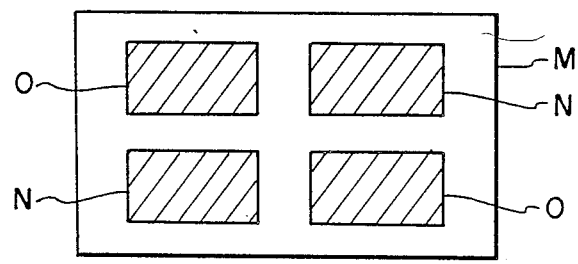
FIG_13
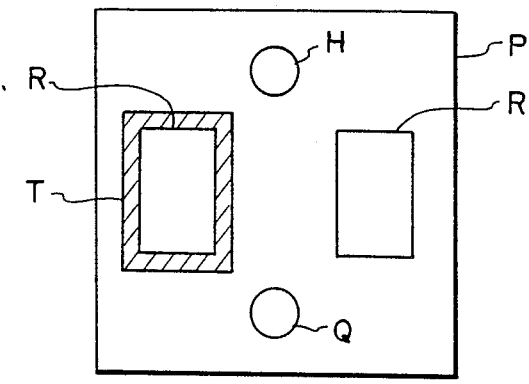

INSECT REPELLENT MATERIAL CONTAINING AMIDE INGREDIENT, CHLORINATED POLYETHYLENE AND ELASTOMER

This is a continuation in part of Ser. No. 07/294,042 filed Jun. 4, 1989 now abandoned which is a continuation in part of Ser. No. 07/091,347 filed Aug. 27, 1987 now abandoned which is a continuation of Ser. No. 06/758,642, filed Jul. 11, 1985, now abondoned.

TECHNICAL FIELD OF THE INVENTION

This invention relates to a repellent material comprising an amide type repelling ingredient, a chlorinated polyethylene and a thermoplastic elastomer, and more particularly to an insect repellent material for preventing insects such as flies, mites, cockroaches and other insects from invading into electronic balances, telephones, computers, facsimiles, automatic vending machines and others in kitchens, foodshops, food storages, foodfirms, or offices, clean rooms, which has an excellent repelling effect to the insects, the repelling effect being controllable for a long period of time in view of using aims.

BACKGROUND OF THE INVENTION

As methods for repelling harmful insects to human bodies, for example, blood-sucking insects as mosquitoes, lice and mites, there is a method in which such chemicals as dimethyl phthalate, 2-ethyl-1,3-hexanediol and indalone are applied to the skin singly or in combination. Recently, as a new type of the insect controlling material, there has been developed an insect controlling sheet comprising a base material such as paper or fabric impregnated or surface-coated with an insecticide. The flies, mites, cockroaches and other insects have been got rid of by scattering the aerosol agents of pyrethroid insecticide or spraying the organic phosphoric insecticide. However, these practices are poor in remaining effects, and so want repetitions. Places treated with the insecticides are polluted and undesirable to the human health, and it is not preferable to use such agents in the places dealing with the foods.

Further, in the food firms of the large scales, fumigation treatments are performed with methyl bromide, chloropicrin or aluminium phosphide. But these chemicals are a powerful medicine and a specific poison and have a high toxicity to men and beasts. Therefore, experts will have to be hired to treat them on holiday and the workers must keep away therefrom for a long time. The above are not easy practices as are ordinarily performed.

Recently there have been developed a repellent material passing a weak electric current, but this is inferior in practice and troublesome in handling.

However, with developing of the standard of living, feeling of cleanness is required, and hence not only intrusion of the insects into places for handling the foods or living spaces but also scatterings of dead bodies of the insects in these places are hated. Moreover, with rapid developments of electronics or the medical industry, a high degree of cleanness is required in precision machines per se or spaces where these precision machines are handled. However, the above-stated insecticidal material for controlling insects often cause scattering of dead bodies of the insects and fail to satisfy the above requirement. Accordingly, a development of a repellent material has been eagerly desired, which has a high effect of preventing the insects from gathering to an applied place, and shows a good durability of this effect and an appropriately controlled chemical releasing property.

In order to enhance the repellent capacity, it is important that the effect of the active chemical should be increased and furthermore the density of the chemical to a base material should be increased and the chemical should be gradually vaporized into an outer space. A product formed by coating a base material with a mixture of a controlling agent and a paint is known. However, the thickness of the coating is limited and even if the repellent chemical is incorporated at a high density, the total amount of the chemical is not increased and the repellent effect is limited. Moreover, if the chemical density is too high, the properties of the coating are degraded. Therefore, there may be assumed a method in which a relatively thick base such as a fabric or paper is impregnated with an active chemical at an appropriate density. According to this method, however, the gradually releasing property cannot be controlled for a long period of time. Therefore, required is a product in which an active chemical is contained in an appropriate amount and the component of a base material has such a chemical and physical affinity with the active chemical that the gradually releasing property is controlled. Moreover, this insect repellent product should be molded into a body capable of agreeing to the shape or configuration of a place or space where the product is set.

As the method for meeting the above requirements, there has been a method in which a repellent, an insecticide, a mildewproof agent, a perfume and the like are incorporated into general purpose thermoplastic resins such as polyethylene, polypropylene and polyvinyl chloride. Moreover, as the method for increasing the density of the active chemical, there has been a method in which chemicals are supported on fillers of these plastics.

These thermoplastic resins have ordinarily a melting point higher than 100° C., and therefore, in a method in which the active chemical is kneaded into a melt of a thermoplastic resin, decomposition or evaporation of the chemical is readily caused. Even if the amount of the chemical to be decomposed or evaporated is small, the amount is increased when the operation is continued for a long period of time, and this method is not practical in view of the safety and efficiency process. For transpiration of the chemical from the surface of the base, it is preferable that the chemical per se should be a substance which is liquid at a room temperature and has a relatively high vapor pressure, and a chemical having a high effect has an especially high transpirability at the room temperature. If a large amount of such a chemical is kneaded into a plastic material having a high melting point, a violent bleeding to the surface is caused simultaneously with decomposition of the chemical.

Under the above mentioned background, the inventors made researches on insect repellent materials, and found that chlorinated polyethylene had a very good affinity with an amide type repelling ingredient of liquid at the room temperature, the content of the active ingredient in the chlorinated polyethylene could be increased, since the chlorinated polyethylene was powdery, it could be impregnated homogeneously with the amide type repelling ingredient, and the chlorinated polyethylene impregnated with the active ingredient could be advantageously formed into good granules for hot molding.

That is, since the chlorinated polyethylene is powdery and has the strong affinity with the amide repelling ingredient, the amide repelling ingredient can be contained much and uniformly, with which a thermoplastic elastomer is mixed. Since the thermoplastic elastomer has less affinity with the amide repelling ingredient than the chlorinated polyethylene, the ratio of the chlorinated polyethylene and the thermoplastic elastomer is controlled, thereby enabling to control the gradually releasing property of the amide type repelling ingredient. Thus, this invention has been accomplished.

DISCLOSURE OF THE INVENTION

The invention has been completed based on a finding that the insect repelling ingredient formed by mixing and hot-molding the chlorinated polyethylene, the amide repellent ingredient and the thermoplastic elastomer can be prepared safely and has a high repelling effect, and the repelling effect can be controlled for a long period of time in view of using aims.

At least one member selected from an amide type repelling ingredient is mixed with chlorinated polyethylene and formed into granules, and the granular mixture is kneaded with the thermoplastic elastomer and hot-molded.

The present repellent material comprises 3 to 40 wt % amide repellent ingredient, 5 to 60 wt % chlorinated polyethylene, and 15 to 80 wt % thermoplastic elastomer, characterized by providing a strong repelling effect and controlling to maintain this effect for a long time.

The amide repelling ingredient: N,N-diethyl-m-toluamide, N-butyl acetoanilide, propyl N,N-diethyl-succinnamate, singly or in combination;

The thermoplastic elastomer: ethylene vinyl acetate copolymer, ethylene propylene copolymer, styrenebutadiene copolymer, 1,2-polybutadiene polymer, polyurethane polymer, preferably melting point of 60° to 100° C.

If the melting point were less than 60° C., the elastomer would be softened at the room temperature, and a shape holding property would be inferior. If it were more than 100° C., the forming temperature had to be raised, and the repellent material is much evaporated at forming products.

In the thermoplastic elastomer the affinity with the repelling ingredient is influenced by chemical properties depending on the molecular chains structure (especially, the side chain and co-monomer of the polymer).

In some elastomers (block copolymers, graft copolymers, random copolymers, homopolymers, blends and chemical modification products), it is considered that various restricted portions (frozen phase, hydrogen bond, crystal phase and ion-crosslinkage) are present in the rubber phase as the non-restricted component, and this structure controls the affinity with the chemical in various manners. Generally, since molecular chains are present in random state in the rubber phase, the rubber phase has the high affinity with the chemical, but since the restricted portion forms aggregates where molecular chains are densely arranged, it is considered that the restricted portion has the low affinity with the chemical. The interfaces between blended polymers forms fine paths for migration of the chemical from the interior of the molded body to the surface.

The chlorinated polyethylene is regarded as an ethylene/vinyl chloride/1,2-dichloroethylene terpolymer, and consists of a crystal phase and a rubber phase according to the degree of crystallinity of starting polyethylene. The restricted crystal phase is a pseudo-lamella hard phase. Chemically, chlorinated polyethylene has the following structure;

showing properties intermediate between those of polyethylene and polyvinyl chloride.

When this powdery chlorinated polyethylene having a degree of crystallinity below 10% is mixed with the above mentioned amide repellent, the repellent is absorbed very well in the chlorinated polyethylene.

If the degree of the crystallinity of the chlorinated polyethylene is not more than 10%, the amide repelling ingredient is absorbed into the chlorinated polyethylene very rapidly, and is not bleeded after the absorption and will be granular, suitable to the forming process. If said degree is more than 10%, the amide repelling ingredient is absorbed thereinto very slowly and will not be granular. Accordingly, the chlorinated polyethylene is preferably used in the invention, where the content of the restricted crystal phase is low, and the content of the rubber phase is high.

With respect to the releasing mechanism of the chemical (i) Amide type repelling ingredient (A)

For example, N,N-diethyl-m-toluamide (DEET) has a structure of

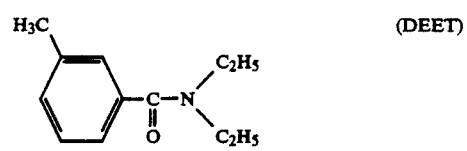

Since this DEET forms a hydrogen bond as shown under in relation with chlorinated polyethylene (B) (CPE), (A) and (B) have good affinity each other

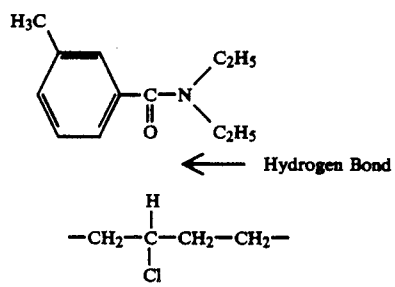

(ii) Solubility parameter is a reference standard of the affinity while kneading the substance composed of (A), (B) and thermoplastic elastomer (C), and if this solubility parameter is calculated with respective units of DEET (A), chlorinated polyethylene (B) and thermoplastic elastomer (C), they show as under

| | | Values of solubility parameters |
|---|---|---|
| DEET (A) 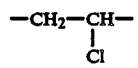 | | 10.7 |
| CPE (B) { Vinyl chloride unit —CH₂—CH—  Cl | | 9.7 |
| 1,2 dichloroethylene unit —CH—CH—  Cl  Cl | | 12.5 |
| Ethylene unit —CH₂—CH₂— | | 7.9 |
| Elastomer (C), e.g., 1,2 polybutadiene —CH₂—CH—  CH=CH₂ | | 8.5 |
| Vynyl acetate of EVA (ethylene vinyl acetate copolymer) —CH₂—CH—  OCOCH₃ | | 9.4 |

With respect to the units of chlorinated polyethylene (B), DEET (A) has the most affinity enriched with the unit of vinyl chloride

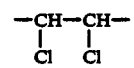

and its affinity becomes lower with 1,2-dichloroethylene unit

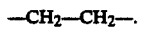

and ethylene unit

—CH₂—CH₂—.

With respect to elastomer, DEET (A) has more or less the affinity of the unit of

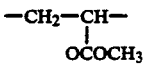

of EVA but has the low affinity with ethylene unit or 1,2-polybutadiene.

In the molecular level the unit having the high affinity with DEET serves as the retaining or holding component, and the unit having the low affinity serves as releasing or breaking component.

That is, due to the difference in the affinity, the releasing mechanism is formed. Further, to say in more macro dimention, the releasing mechanism is formed in the passing pathes in the boundaries of the blended polymers.

Thus, the releasing mechanism is formed in the molecular level and the macro level.

Actually, the releasing is carried out as follows. DEET has vapor pressure of $1.5 \times 10^{-3}$ mmHg at 25° C., and since this vapor pressure is relatively high, DEET is easily volatile, and therefore DEET volatilizes gradually into the air from the surface of the repellent material. Subsequently, the density of DEET around the surface of the product becomes low, and DEET moves from the interior thereof nearly to the surface due to the diffusion mechanism by the difference in density. This diffusion rate may be controlled in view of the product using purpose by change in the structure of said molecular level.

The releasing rate of N,N-diethyl-m-toluamide may be controlled for a long period of time by using the above stated releasing mechanism. In other words, if the ratio of the units having the low affinity with N,N-diethyl-m-toluamide is increased, its releasing rate is heightened, and if the ratio of the unit having the high affinity therewith is increased, its releasing rate is lowered.

If the amide repellent ingredient is added more than 1 wt % to the whole of insect repelling material, a sufficient effect is shown, and actually, 3 to 40 wt % is preferable in view of the continuity and the cost. If the density of the amide repellent is less than 3 wt %, the continuity of the repelling effect is poor, and if it is more than 40 wt %. the content of the liquid is too much and it is difficult to make granular materials suitable to the forming process.

The chlorinated polyethylene may be changed in accordance with the amount of the amide repelling ingredient. In general, it is reasonable to add the chlorinated polyethylene of around 5 to 35 wt % for the amide repelling ingredient of 3 to 20 wt %, and the former of around 35 to 60 wt % for the latter of 20 to 40 wt %, and the amount of the former may be, if necessary, changed in response to the sort of the thermoplastic elastomer and the releasing speed of the latter.

The mixture of the amide repellent ingredient, the chlorinated polyethylene and the thermoplastic elastomer can be formed in sheet, net, rod and other shapes by a known thermal forming machine.

If the shape is a sheet, it may be laminated with a substance which does not penetrate amide repelling ingredient, such as a film of PET (polyethylene terephthalate) vacuum-deposited with aluminium or aluminium foil, so that the amide repelling ingredient is released from a remaining side, and at the same time, the attaching side of the insect repelling ingredient is prevented from influences by the amide repelling ingredient. As the cases may be, it is sufficient that the sheet is applied to its one side with a substance of not penetrating the amide repelling ingredient, and is laminated to the other side with a material penetrating the amide repelling ingredient such as a film of pierced PET, pierced aluminium foil, or the cloth or paper. Further, the sheet may be laminated with the material of penetrating the amide repelling ingredient to one side.

BRIEF DESCRIPTION OF THE DRAWINGS

FIG. 1 is a view showing an example of laying the sheet of the insect repellent material;

FIG. 2(A) and 2(B) are partially enlarged views of the sheets of the insect repellent material according to one embodiment;

FIG. 3 is a view showing an example of attaching the insect repellent material to legs of an automatic vending machine;

FIG. 4 is an enlarged plane view of the insect repellent material of FIG. 3;

FIG. 5 is a cross sectional view of the product for the automatic vending machine of FIG. 4;

FIG. 6 is an enlarged cross sectional view where an aluminium foil is perforated in the product of FIG. 4;

FIG. 7 is a cross sectional view of another embodiment of the product to the attached to the legs of the automatic vending machine;

FIG. 8 is a perspective view of the insect repellent material;

FIG. 9 is a view showing the product attached to a pipe of a building;

FIG. 10 is a schematic view showing a method of testing a repelling effect (Selection Box Method);

FIG. 11 is a schematic view showing another method of testing a repelling effect (Eaten Bait Comparison Method);

FIG. 12 is a schematic view showing a further method of testing a repelling effect (Shelter Method); and FIG. 13 is a schematic view showing a still further method of testing a repelling effect (Pseudo Practice Method).

MOST PREFERRED EMBODIMENT FOR PRACTICING THE INVENTION

The present invention will now be described with reference to embodiments illustrated in the accompanying drawings.

In FIG. 1, a reference numeral 1(A) is an insect repellent sheet, B designates a bed on which a balance is placed.

Referring to FIG. 2(A), a sheet-like insect repellent material 1 comprises a gradually releasing base 2 formed by mixing chlorinated polyethylene, 1,2-polybutadiene, an ethylene/vinyl acetate copolymer or an ethylene/propylene terpolymer as a thermoplastic elastomer, an inorganic filler and N,N-diethyl-m-toluamide as an amide type repelling ingredient and molding the mixture into a sheet and an aluminium foil 3 or a PET film having an aluminium foil vacuum-deposited thereon, which is bonded to one surface of the base 2 as the sticking-preventing layer.

FIG. 2(B) shows that the material of FIG. 2(A) is laminated on its surface 1 with the amide repellent penetrating film, and the reference numeral 31 is an aluminium foil, and 7 is holes formed thereon.

In FIG. 3, D designates an automatic vending machine, and 4 is the insect repellent material.

In FIG. 4, the sheet of FIG. 2(A) is cut into a regular square and the insect repellent material only is cut into a circular hole 5 to meet the size of the leg of the vending machine, and the remaining aluminium foil 3 is formed with notches and is bent inwardly and is cut at 6 to catch the leg.

In FIG. 6, the amide repellent ingredient evaporates from the surface 4 and through the holes 7.

In FIG. 7, the numeral 8 designates a face for evaporating the repellent ingredient.

In FIG. 8, the numeral 9 is a hole for catching the leg E, and 10 is a cutline for the leg.

In FIG. 9, F is a pipe of a building.

In FIG. 10, A is a plastic box, B is a partition wall, C is a control sheet not containing the repellent material and T is a sheet of the insect repellent ingredient.

In FIG. 11, G is a plastic container, H is a container supporting the water, I is a shelter, J are cubic sugars and K is is a net of the insect repellent material and L is a control net not containing the repellent ingredient.

In FIG. 12, M is a plastic container, N is a shelter laid with the net having the repellent ingredient and 0 is a shelter laid with the control net not containing the repellent ingredient.

In FIG. 13, P is a tin made vat, H is a container supporting the water, Q is a container holding a bait, R is a precision chemical balance and T is a sheet of the repellent material.

This sticking-preventing layer may be a material not allowing permeation of the amide repelling ingredient transpirated from the gradually releasing base, such as a metal foil, especially a metal foil (particularly aluminium) vacuum-deposited on a synthetic resin film such as PET, or a material allowing permeation of the chemical but not adhering to the setting surface, for example, a Japanese paper, non-woven fabric, glassfiber or metal net, or a material coated with an inorganic substance. If a layer having a metallic gloss is formed by using a material as mentioned above and the insect repellent material is arranged so that this layer is directed to the insect intrusion side, since the insects have an inclination of avoiding a light place, they do not come near to the insect repellent material because they avoid light reflected from the metallic gloss surface, and therefore, the repelling effect is double by this effect and the effect of the repellent material per se. In the case where layers formed of a sticking-preventing material are formed on both the surfaces of the gradually releasing base, it is indispensable that at least one layer should be formed of a material allowing permeation of the active ingredient. If the layer is formed of a material not allowing permeation of the active ingredient, the layer may be perforated so that the active ingredient can permeate through the layer.

The insect repellent material 1(A) is placed on a foundation bed B so that the aluminium foil 3 is located below, as shown in FIG. 1. If a balance C is placed on the repellent material 1(A), the intrusion of the insect into the balance C is prevented by the amide repelling ingredient transpirated from the gradually releasing base 2, and bleeding of the amide repelling ingredient of the gradually releasing base 2 to the foundation bed B is prevented by the aluminium foil 3. Therefore, even if the insect repellent material 1 is allowed to stand still in this state for a long time, sticking of the insect repellent material 1 to the foundation bed B, rendering detachment thereof difficult, can be prevented.

In the present embodiment, if the aluminium foil 3 having holes 7 of an appropriate size is bonded to the top surface of the gradually releasing base 2 as shown in FIG. 2(B), sticking of the bottom surface of the balance C to the insect repellent material 1(A) can be prevented while the transpiration of the active ingredient is accomplished through the holes 7 and intrusion of the insects can be prevented assuredly by the light reflected by the aluminium foil 3.

FIGS. 2 through 5 show another embodiment of the insect repellent material 4 having a square shape which is attached to an intermediate portion of a leg E of an automatic food vending machine D. This insect repellent material 4 is formed by cutting the above mentioned insect repellent material 1 into a square shape, forming a hole 5 to be fitted to the leg E while leaving the aluminium foil 3 unperforated, forming one cut line 6 extending between the peripheral edge and the hole 5 for attachment of the insect repellent 4 to the leg E and forming a plurality of cut lines 6 in the portion 3a, exposed to the hole 5, of the aluminium foil 3. This insect repellent 4 is arranged so that the aluminium foil 3 is located below, and as shown in FIG. 5, the material 4 is attached to the leg E in the state where the portion, exposed to the hole 5, of the aluminium foil 3 is bent to cover the inner circumference of the hole 5. Sticking of the insect repellent material 4 to the leg E is prevented, and because of the gloss of the aluminum foil 3, the gathering of the insects is prevented, and even if the insects go beyond this aluminium foil 3, further intrusion is prevented because of the gradually releasing base 2. Thus, the intruction of the insects is doubly prevented.

If holes 7 having an appropriate size are formed at appropriate intervals on the aluminium foil 3 as the lower surface of the insect repellent material 4 as shown in FIG. 6, since the active ingredient is gradually released from the holes 7, an effect of preventing the gathering of the insects is enhanced, and also an effect of preventing the gathering of the insects is attained by reflection of the light. In a case where the thickness of the gradually releasing base 2 is so small that sticking to the leg E is not caused, there may be a method in which the aluminium foil 3a is cut off from the portion of the hole 5 and the inner circumferential surface of the hole 5 is directly contacted with the leg E. Incidentally, even if the insect repellent material 1 having the holes 7 formed in the aluminium foil 3 is used as shown in FIG. 1, since the aluminium foil 3 is present on the surface to be pressed to the foundation bed B, the sticking is prevented.

FIGS. 7 and 8 show a modification of the insect repellent material to be attached to the leg E. This insect repellent material 8 is formed to have a frustoconical shape, and a layer of a metal film such as the aluminium foil 3 is formed on the lower surface, that is, the inner circumferential surface. Reference numeral 9 represents a fitting hole to the leg E, reference numeral 10 represents a cut line for fitting, and reference numeral 3a represents an aluminium foil covering the inner circumferential surface of the fitting hole 9. In this insect repellent material 8, the insects should pass through an inclined surface of a reverse mountation shape of the aluminium foil 3 for intruction, and therefore, a passage of the insects is substantially impossible and the effect of preventing intrusion of the insect is very high. Also in this embodiment, the holes 7 may be formed on the aluminium foil 3.

If the above-mentioned insect repellent material 4 or 8 is attached to the midway of a column F or a tree as shown in FIG. 9, intrusion of the insects into a building or fruit tree from the ground can be prevented.

The present invention will now be described in detail with reference to the following examples.

EXAMPLE 1

N,N-diethyl-m-toluamide was incorporated as a repelling ingredient into 300 parts by weight of the chlorinated polyethylene (marketed under the trade name of "Daisolac H-135" by Osaka Soda Co., Ltd.) so that the mixing ratio of the amide repelling ingredient to the polymer blend was as shown in Table 1 given below, and the mixture was appropriately granulated by a vertical granulator. Then, the granulation product was mixed with a mixed pellet comprising 300 parts by weight of 1,2-polybutadiene (marketed under the trade name of "JSR RB-810" by Japan Synthetic Rubber Co., Ltd.), 200 parts by weight of an ethylene/vinyl acetate copolymer (marketed under the trade name of "Ultrathene UE-634" by Toyo Soda Co., Ltd.) and 300 parts by weight of an ethylene/propylene copolymer (marketed under the trade name of "Tufmer P-0280" by Mitsui Petroleum Chemical Industry Co., Ltd.) and the mixture was extruded at 95° to 100° C. by using an extruder to obtain the insect repelling material in the form of a sheet having a thickness of 2 mm.

Changes of the cockroach repellent rate and the active ingredient residual ratio with the lapse of time in this sheetlike insect repellent material were examined. The obtained results are shown in the following Table 1:

TABLE 1

| Mixing Ratio (% by weight) of Repellent Ingredient | Initial Repellent Rate (%) | 2 Weeks | | 1 Month | | 2 Months | |
|---|---|---|---|---|---|---|---|
| | | Residual Ratio (%) | Repellent Rate (%) | Residual Ratio (%) | Repellent Rate (%) | Residual Ratio (%) | Repellent Rate (%) |
| 4 | 90 | 96 | 96 | 79 | 80 | 58 | 87 |
| 6 | 97 | 97 | 100 | 73 | 93 | 60 | 87 |
| 8 | 99 | 94 | 99 | 64 | 96 | 67 | 88 |
| 10 | 98 | 98 | 100 | 60 | 96 | 62 | 91 |

In the above Table 1, the repellent rate was determined according to a following method A partition wall B was formed at the center of a vat A (1 m square and 80 cm depth) shown in FIG. 10, and a passage b having a width of 10 cm and a height of 5 cm was formed in the lower central part of the partition wall B. A sheet T of 1 m width and 80 cm length containing the repelling ingredient was set on the wall of one room and a sheet C of 1 m (width)×80 cm (length) free of the repelling ingredient was set on the wall of another room to define these rooms T and C. Then, 30 imaginal German cockroaches were set free substantially at the center of the partition wall B and after the lapse of two hours, the number of cockroaches present in the room C and room T was counted and the ratio was calculated as the repellent rate. The repellent rate was calculated as follows.

$$\text{Repellent Rate} = \frac{A - B}{A} \times 100$$

A: The number of cockroaches in Room C
B: The number of cockroaches in Room T

EXAMPLE 2

30 parts by weight of N,N-diethyl-m-toluamide was added to 100 parts by weight of chlorinated polyethylene (Trade Name: Daisolac H135 by Osaka Soda Co., Ltd.), and mixed and granulated by the vertical granulator. Then, 300 parts by weight of ethylene vinyl acetate copolymer (Trade Name: Ultrathene UE630 by Toyo Soda Co., Ltd.) was mixed and the mixture was extruded at 95° to 100° C. by an extruder, and a net of knot being 4 mm and weight being 130 g/m² was produced.

The repelling rate of the cockroaches and the residual ratio of N,N-diethyl-m-toluamide with respect to the initial repellent as the time passed are as shown in a following Table 2:

TABLE 2

|  | Initial | 3 Weeks | | 3 Months | | 6 Months | |
| --- | --- | --- | --- | --- | --- | --- | --- |
|  | Repellent Rate (%) | Residual Ratio (%) | Repellent Rate (%) | Residual Ratio (%) | Repellent Rate (%) | Residual Ratio (%) | Repellent Rate (%) |
| Ex. 2 | 99.6 | 83 | 99.2 | 41 | 97.5 | 23 | 90.4 |

In the above Table 2, the repellent rate was determined according to a following method.

The water and the shelter were positioned in the plastic container (20 cm×40 cm) shown in FIG. 11. The net of Example 2 and the control net (not containing the amide repellent) made in the same manner as in Example 2 were positioned and the cubic sugars precisely weighted were positioned at the center of the net. 100 imaginal German cockroaches were released in the container, and after 4 days the reduced weights of the cubic sugars were obtained, and the repellent rate was calculated as follows.

$$\text{Repellent Rate} = \frac{A - B}{A} \times 100$$

A: The amount of weight reduction of sugar on the control net
B: The amount of weight reduction of sugar on the net of Example 2

EXAMPLE 3

30 parts by weight of N,N-diethyl-m-toluamide was added to 100 parts by weight of chlorinated polyethylene (Trade Name: Daisolac H135 by Osaka Soda Co., Ltd.), and mixed and granulated by the vertical granulator. Then, 70 parts by weight of ethylene vinyl acetate copolymer (Trade Name: Ultrathene UE630 by Toyo Soda Co., Ltd.) was mixed and the mixture was extruded at 95° to 100° C. by an extruder, and a net of knot being 15 mm and weight being 200 g/m² was produced.

The repelling rate of the cockroaches and the residual ratio of N,N-diethyl-m-toluamide with respect to the initial repellent as the time passed are as shown in a following table 3.

TABLE 3

|  | Initial | 3 Weeks | | 3 Months | | 6 Months | |
| --- | --- | --- | --- | --- | --- | --- | --- |
|  | Repellent Rate (%) | Residual Rate (%) | Repellent Ratio (%) | Residual Rate (%) | Repellent Ratio (%) | Residual Rate (%) | Repellent Ratio (%) |
| Ex. 3 | 100 | 79.4 | 99.7 | 47.5 | 99.3 | 32.1 | 98.3 |

In the above Table 3, the repellent rate was determined according to the following method.

Four shelters were positioned in the plastic container (40 cm width and 70 cm length) shown in FIG. 12. The nets of Example 3 were laid in the two of the shelters and the control nets (not containing the amide repellent) made in the same manner as in Example 3 were laid in the other two shelters, and 100 imaginal German cockroaches were released in the container, and after 24 hours the number of the cockroaches was counted, and the repellent rate was calculated as follows.

$$\text{Repellent Rate} = \frac{A - B}{A} \times 100$$

A: The number of cockroaches within the shelter having the control net laid
B: The number of cockroaches within the shelter having the net of Example 3 laid

EXAMPLE 4

40 parts by weight of N,N-diethyl-m-toluamide was added to 100 parts by weight of chlorinated polyethylene (Trade Name: Daisolac H135 by Osaka Soda Co., Ltd.), and mixed and granulated by the vertical granulator. Then, 20 parts by weight of 1,2-polybutadiene and 20 parts by weight of ethylene vinyl acetate copolymer were mixed and extruded at 95° to 100° C. by the extruder, and the insect repelling materials of 1.5 mm were produced in sheet. The repelling rate of the cockroaches and the residual ratio of N,N-diethyl-m-toluamide with respect to the initial repellent as the time passed are as shown in a following Table 4.

TABLE 4

|  | 3 Days | | 1 Week | | 2 Weeks | |
| --- | --- | --- | --- | --- | --- | --- |
|  | Residual Rate (%) | Repellent Ratio (%) | Residual Rate (%) | Repellent Ratio (%) | Residual Rate (%) | Repellent Ratio (%) |
| Ex. 4 | 98.5 | 100 | 97.2 | 98.8 | 94.4 | 92.6 |

In the above Table 4, the repellent rate was determined according to the following method.

The water and bait were placed in the tin made vat (1.5 m square) shown in FIG. 13, and 50 imaginal German cockroaches and 50 larva ones were released in a day and night, and two of the precise chemical balances were positioned as seen in FIG. 13. One of the balances was set on the sheet of Example 4, and the other balance was set directly on the vat. After a certain time passed, the number of the cockroaches within the balances was counted, and the repellent rate was obtained as follows.

$$\text{Repellent Rate} = \frac{A - B}{A} \times 100$$

A: The number of cockroaches within the non-treated weighting balance
B: The number of cockroaches within the weighting balance having the sheet of Example 4 laid

What is claimed is:

1. An insect repellent consisting of a material made by mixing 3 to 40 wt. % amide repelling ingredient and 5 to 60 wt. % chlorinated polyethylene of crystallinity of not more than 10%, to form granules, and then mixing the granules with 15 to 80 wt. % thermoplastic elastomer having a melting point of between 60° to 100° C., and then hot holding to thereby provide a gradually released repelling effect; wherein said amide repelling ingredient is selected from the group consisting of N,N-diethyl-m-toluamide, N-butyl acetoanilide, and N,N-diethyl succinamate, and mixtures thereof; and wherein said thermoplastic elastomer is selected from the group consisting of ethylene vinyl acetate copolymer, ethylene propylene copolymer, styrene butadiene copolymer, 1,2-polybutadiene polymer and polyurethane polymer.

2. The repellent of claim 1, wherein said repelling effect is at a repelling rate of at least 90 % for at least six months at room temperature.

3. An insect repellent consisting essentially of a material produced by a process comprising the steps of
    first, homogeneously impregnating 3 to 40 wt. % liquid amide repelling ingredient into 5 to 60 wt. % powdery chlorinated polyethylene of crystallinity of not more than 10%, to form granules;
    second, kneading the resulting granules with 15 to 80 wt. % thermoplastic elastomer having a melting point of between 60° to 100° C.; and
    finally, hot molding the resulting kneaded mixture to thereby produce a solid repellent material wherein the amide repelling ingredient is gradually released so as to result in an insect repelling rate of at least 90 % for at least six months at room temperature;
    wherein said amide repelling ingredient is selected from the group consisting of N,N-diethyl-m-toluamide, N-butyl acetoanilide, and N,N-diethyl succinamate, and mixtures thereof; and
    wherein said thermoplastic elastomer is selected from the group consisting of ethylene vinyl acetate copolymer, ethylene propylene copolymer, styrene butadiene copolymer, 1,2-polybutadiene polymer and polyurethane polymer.

4. An insect repellent material consisting essentially of granules prepared by mixing 1 to 50 percent by weight of an active ingredient selected from the group consisting of N,N-diethyl-m-toluamide, N-butylacetoanilide, and propyl N,N-diethyl succinamate, and 20 to 70 percent by weight of chlorinated polyethylene; said percent being based on amount of thermoplastic elastomer; and said thermoplastic elastomer being in an amount to satisfy said percents kneaded with said granules with the kneaded product being subjected to hot molding, said elastomer having a melting point of 60° to 100° C. and said chlorinated polyethylene having a high rubber phase content and an affinity for and retention of said active ingredient; wherein said chlorinated polyethylene absorbs the active ingredient, and the elastomer gradually breaks down the affinity and retention of the active ingredient by the chlorinated polyethylene, thereby to gradually release the active ingredient.

5. A device comprising a base and coated on said base the insect repellent material of claim 4.

* * * * *